United States Patent [19]

Pesa et al.

[11] Patent Number: 4,652,677

[45] Date of Patent: Mar. 24, 1987

[54] SELECTIVE HYDROCARBOXYLATION OF PROPYLENE TO ISOBUTYRIC ACID

[75] Inventors: Frederick A. Pesa, Aurora; Thomas A. Haase, University Hts., both of Ohio

[73] Assignee: The Standard Oil Company, Cleveland, Ohio

[21] Appl. No.: 128,602

[22] Filed: Mar. 10, 1980

[51] Int. Cl.[4] ................. C07C 51/14; C07C 51/145
[52] U.S. Cl. ................................................. 562/522
[58] Field of Search ........................................ 562/522

[56] References Cited

U.S. PATENT DOCUMENTS

| | | | |
|---|---|---|---|
| 2,593,440 | 4/1952 | Hagemeger et al. | 562/522 |
| 3,437,676 | 4/1969 | von Kutepow et al. | 562/522 |
| 3,450,730 | 6/1969 | Scheben et al. | 260/429 |
| 3,501,518 | 3/1970 | von Kutepow et al. | 562/522 |
| 3,641,074 | 2/1972 | Fenton | 260/410.9 R |
| 3,654,322 | 4/1972 | Fenton | 260/546 |
| 3,661,949 | 5/1973 | Fenton | 260/413 |
| 3,668,249 | 6/1972 | Fenton | 260/546 |
| 3,725,305 | 4/1973 | Wilkinson | 252/429 R |
| 3,816,490 | 6/1974 | Forster et al. | 260/413 |
| 3,819,669 | 6/1964 | Knifton | 260/410.9 R |
| 3,855,307 | 12/1974 | Rony et al. | 560/232 |
| 3,856,856 | 12/1974 | Nozaki | 562/519 |
| 3,857,900 | 12/1974 | Wilkinson | 560/233 |
| 3,892,788 | 7/1975 | Knifton | 260/410.9 R |
| 3,919,272 | 11/1975 | Knifton | 260/410.9 R |
| 3,933,919 | 1/1976 | Wilkinson | 562/522 |
| 3,968,133 | 7/1976 | Knifton | 260/410.9 R |
| 4,245,115 | 1/1981 | Butter | 560/233 |
| 4,354,978 | 10/1982 | Frampton et al. | 562/522 |

FOREIGN PATENT DOCUMENTS 2739096 3/1978 Fed. Rep. of Germany .

*Primary Examiner*—Werren B. Lone
*Attorney, Agent, or Firm*—Teresan W. Gilbert; Joseph G. Curatolo; Larry W. Evans

[57] ABSTRACT

A process for the selective hydrocarboxylation of propylene to produce predominantly isobutyric acid in the liquid phase is provided. The reaction of propylene, carbon monoxide and water is effected at a temperature of about 75° C. to about 150° C. and at a pressure of about 250 psi to about 5000 psi in the presence of a suitable solvent and a catalyst comprising palladium or a palladium compound supported on an inert carrier, an organo-arsine ligand compound and a hydrogen halide.

39 Claims, No Drawings

SELECTIVE HYDROCARBOXYLATION OF PROPYLENE TO ISOBUTYRIC ACID

BACKGROUND OF THE INVENTION

This invention relates to the hydrocarboxylation of olefins to form carboxylic acids. More specifically, this invention relates to the hydrocarboxylation of propylene with CO and $H_2O$ in the liquid phase to produce butyric acid, wherein the isobutyric acid isomer product predominates. The isobutyric acid may then be dehydrogenated to produce methacrylic acid.

Conventionally, hydrocarboxylation of olefins has been intended to produce predominantly the linear, straightchain or normal (n) isomer of the carboxylic acid desired. U.S. Pat. No. 3,641,074 to Fenton discloses the preparation of normal or straight chained carboxylic acids, esters and anhydrides via the carbonylation of olefins in the presence of a Group VIII noble metal in complex association with a biphyllic ligand. Suitable ligands may include triarylphosphine and triarylarsine among others.

U.S. Pat. No. 3,816,490 to Forster et al. discloses the production of carboxylic acids by carboxylation of olefins, utilizing a Group VIII metal compound, preferably cobalt, rhodium and iridium together with a phenolic promoter compound. The metal compound may be elemental metal, a simple salt, or an organometallic complex. The reaction yields predominantly normal carboxylic acids when isomeric products are to be prepared.

U.S. Pat. Nos. 3,857,900 and 3,933,919 to Wilkinson disclose hydrogenation, hydroformylation and carbonylation reactions resulting primarily in the formation of linear products when catalysts comprising platinum group metals, ligands containing nitrogen, phosphorus, arsenic or antimony; and a halogen or pseudo-halogen are utilized.

U.S. Pat. Nos. 3,919,272 and 3,968,133 to Knifton disclose the preparation of linear fatty acids and esters from olefins, carbon monoxide and alcohols or water in the presence of ligand-stabilized palladium halide complexes in combination with a halide salt of either tin or germanium. Ligands may include phosphines, and arsines among others.

The preparation of increased ratios of branchedchain or iso-carboxylic acids to straight-chain acids is described in U.S. Pat. No. 3,661,949 to Fenton. Olefins are hydrocarboxylated in the presence of a biphyllic ligand-stabilized Group VIII noble metal compound catalyst and an iron halide co-catalyst. The ligand may include arsines or phosphines, among others.

West German Offenlegungsschrift No. 2,739,096 describes the preparation of isobutyric acid esters by the carbonylation of propylene with carbon monoxide and an alcohol in the presence of a palladium salt, a triarylarsine, and a halogen acid. An amount of water larger than about 0.1 mole per mole of propylene is described as being harmful to the carbonylation reaction.

U.S. Pat. No. 3,501,518 to Kutepaw et al. discloses the preparation of carboxylic acids or esters from olefins utilizing a supported or nonsupported catalyst comprising metallic palladium or a palladium chalcogenide, an acid and an organic phosphine or nitrile.

U.S. Pat. No. 3,855,307 to Rony et al. discloses multiphase catalysts comprised of a porous solid carrier upon which a liquid-phase catalyst is disposed. Such catalysts are useful for hydroformylation and carbonylation reactions. The exemplified reactions demonstrate that the products obtained are predominantly composed of normal-chain hydrocarbons.

In general the above described catalyst systems are non-selective for the "iso" form of the carboxylic acid products, tending to yield predominantly straight chain products. The catalyst systems described above for use in hydrocarboxylation are often susceptible to deactivation due to the transformation of the Group VIII metal ion particularly palladium, contained therein to either a nonselective or a nonreactive form by the action of the carbon monoxide reactant. These systems may also present difficulties in the separation of the solubilized catalyst from the liquid reaction products. Any catalyst system to be utilized in the hydrocarboxylation reaction must be thermally stable at the temperatures required for the reaction to effectively occur. Other factors which effect the hydrocarboxylation reaction are the molar ratios of the catalyst metal component to stabilizing ligands, to the reactants, and to other components of the system.

SUMMARY OF THE INVENTION

It is therefore an object of the present invention to provide a process for the hydrocarboxylation of propylene in the liquid phase, to produce butyric acid.

It is a further object of the present invention to provide a process for the hydrocarboxylation of propylene in the liquid phase to produce predominantly the isobutyric acid isomer product.

It is a further object of the present invention to provide a process for the hydrocarboxylation of propylene in the liquid phase to produce isobutyric acid utilizing an active palladium catalyst system which is thermally stable, and which does not readily lose selectivity at the reaction temperatures required.

It is a further object of the present invention to provide a process for the hydrocarboxylation of propylene in the liquid phase to produce isobutyric acid utilizing an active palladium catalyst system supported on an inert carrier.

These and other objects of the present invention, together with the advantages thereof, which shall become apparent from the specification that follows, are accomplished by the invention as hereinafter described and claimed.

In general, the process of the present invention includes the preparation of predominantly isobutyric acid in the liquid phase. A reaction mixture is formed from propylene, carbon monoxide and water in a suitable solvent in the presence of a supported, active palladium catalyst system. The reaction mixture is subjected to a temperature of about 75° C. to about 150° C. and a pressure of about 250 psi to about 5000 psi. The catalyst system generally includes palladium or a palladium compound supported on an inert carrier, an organoarsine ligand-forming compound and a hydrogen halide.

DETAILED DESCRIPTION OF THE INVENTION

The preparation of the iso or branched isomer of butyric acid from propylene, carbon monoxide and water in the liquid phase proceeds according to the following catalyzed reaction.

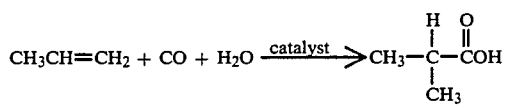

The formation of n-butyric acid, in which all the carbon atoms form a straight chain, is to be minimized to the greatest extent possible.

The production of predominantly the "iso" form of butyric acid is made possible by the choice of catalyst system, including stabilizing and promoting ligands and complexing acids, and by the choice of the physical form of the catalyst system. We have found that other factors which contribute to the unexpected predominance of our desired isomer product include the amount of stabilizing ligand with respect to the catalytic metal compound utilized, and the ratio of the amount of propylene fed in the reaction to the amounts of catalyst and solvent present. Still other factors to be considered are reaction temperature, pressure and complexing acid concentration.

The following reaction mechanism has been proposed for the preparation of isobutyric acid from propylene, carbon monoxide and water. This mechanism is merely theoretical and in no manner is intended to limit the scope of the present invention, but rather is provided to illustrate the subject reaction.

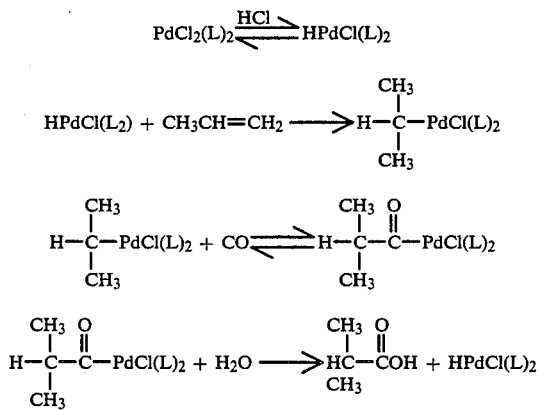

The catalyst system according to the present invention includes ligand-stabilized and ligand-promoted, palladium or palladium compound supported on an inert carrier, together with a complexing hydrogen halide acid, preferably hydrochloric acid, optionally with other strong acids, preferably in addition to HCl.

The palladium or palladium compound utilized according to the present invention is capable of coordinating carbon monoxide, propylene and water as is demonstrated in the reaction mechanism above. It is preferred that the palladium component of the catalyst be impregnated upon the inert support as a solution of a palladium salt in the +2 valence state. Suitable palladium salts include Pd(acetate)$_2$, PdCl$_2$, Pd(NO$_3$)$_2$ and the like. The molar ratio of propylene fed in the reaction to the palladium present, whether in a batch-type reaction or a continuous reaction, is about 10:1 to about 2000:1, preferably about 100:1.

The catalyst system may include, in addition to palladium, metals or metal compounds selected from Groups VIIA, VIII, IB and IIIB of the periodic table (Periodic Table as appearing in "Advance Inorganic Chemistry", Cotton and Wilkinson, 3rd Ed.), including, but not limited to, rhenium, silver, gold and thallium, which are preferred. Most preferred are Group IB metals, particularly silver and gold. The molar ratio of the additional metals to the palladium present is within the range of about 0.5:1 to about 5.0:1, preferably within the range of about 1:1 to about 2.5:1.

The carrier material utilized should be essentially inert under the reaction conditions employed. Suitable examples of essentially inert support materials include: Alundum (Norton), silica, alumina, alumina-silica, silicon carbide, titania, zirconia, carbon and zeolites such as molecular sieves. Other types of suitable carriers may also be utilized according to the present invention, provided that they are at least partially porous, being susceptible to the penetration of liquid. The carrier material may have any shape, such as spheres, rings or irregular shapes which provide a higher surface area per unit weight of support.

The amount of palladium present on the carrier material utilized should be about 0.01% to about 30% by weight palladium, based upon the total weight of the palladium compound and carrier. A preferred catalyst/carrier composite contains about 0.05% to about 10% by weight palladium, and a most preferred catalyst/carrier composite contains about 0.1% to about 5% by weight palladium.

The palladium component of the catalyst system, that is, the palladium or palladium compound supported on the carrier material, may be easily separated from the reactants, products and solvent by conventional methods, such as filtration, and thus can be reused in subsequent reactions.

The transformation of the palladium catalyst which is selective to the production of isobutyric acid to a nonselective form is inhibited in part by the incorporation of stabilizing ligands in the catalyst system. Stabilizing ligands which function effectively as promoters to the subject reaction include arsines of the general formula

where R$_1$, R$_2$ and R$_3$ are independently a substituted or unsubstituted alkyl, aryl, alkoxy or aryloxy group. It is preferred that at least one R be an aryl group or a substituted aryl group which is stable and at least partially unreacted during the course of the reaction. The substituent on the substituted aryl group may be lower alkyl, alkoxy, acid, ester, carbonyl, aromatic, halide, cyanide or the like, where the substituent is in the meta and/or para position. Triarylarsines, particularly triphenylarsine, are preferred stabilizing/promoting ligands. Diarsines and triarsines may also be used, however, rates of reaction are generally considerably slower when using these compounds. The molar ratio of AsR$_3$/Pd according to the present invention is within the range of about 1:1 to about 100:1, and preferably is in the range of about 2:1 to 20:1.

The catalyst system requires a hydrogen halide which is capable of being coordinated with the palladium metal ion. Hydrogen chloride is preferred and may be supplied to the reaction in aqueous or anhydrous form or as a compound which is capable of releasing HCl under the reaction conditions. HBr and HI can also be used, but the activity of the catalyst system is lower when these are used alone. Mixtures of HCl and HBr or HCl and HI are also used to lend stability to the system. Other strong acids may be added to the system as a complexing acid in addition to the hydrogen halide, such as $H_2S$, $H_2SO_4$, HCN, $H_3PO_4$ and $HBF_4$.

The halide component of the hydrogen halide should be present in a molar ratio of about 5:1 to about 500:1 with respect to the palladium in the system. A preferred ratio of HCl/Pd is from about 45:1 to about 90:1, throughout which range conversion and selectivity to isobutyric acid increase. The HCl/Pd ratio of 90:1 is most preferred. The molar ratio of propylene fed in the reaction to the halide component present is preferably within the range of about 10:1 to about 1000:1.

Suitable solvents according to the present invention include inert organic solvents such as benzene or substituted aromatic compounds, carboxylic acids such as acetic acid, esters, ethers such as dioxane, aldehydes, ketones and the like. The product acid may also be utilized as the solvent.

The reaction of propylene, carbon monoxide and water in the presence of the ligand-stabilized palladium catalyst should be conducted at a temperature in the range of about 75° C. to about 150° C. Preferred temperatures are within the range of about 90° C. to about 125° C. At low temperature, the rate of reaction is unacceptably slow, and at temperatures higher than about 150° C. the catalyst system is generally unstable.

The molar ratio of water to propylene in the reaction medium should be maintained within the range of about 0.01:1 to about 2:1. It is preferred that the molar ratio of water to propylene be maintained at about 1:1 to about 2:1.

The reaction should be carried out under a carbon monoxide pressure of about 250 psi to about 5000 psi. Preferred CO pressures are from about 400 psi to about 1200 psi. It has been found that maintaining the reaction at these pressures results in a great increase in the rate of reaction, an increase of selectivity to isobutyric acid, no palladium deactivation and decreased isopropylchloride byproduct production. Maintaining the reaction at high pressure additionally allows a greater throughput to desired products per unit of time.

SPECIFIC EMBODIMENTS OF THE INVENTION

A series of exempletive reactions were carried out in a 300 ml Hastelloy C autoclave in pyrex glass liners. Although the examples were carried out as batch-type reactions to illustrate the present invention, it is intended that the scope of the present invention include continuous feed-type reactions also. Analysis of liquid product was performed on a Hewlett-Packard 5710 A gas chromatograph. Valeric acid was used as the internal standard, and column packing was Polyester FF (trademark of Nishio Industries). Analysis of gases was performed on a Carle III gas analyzer using a Houdry dual column with thermisters as detectors.

The reaction in the examples set forth below were run in the following manner. A pre-weighed amount of palladium-impregnated carrier, promoter ligand, solvent, water and hydrogen halide was placed into the glass liner. The palladium or palladium containing compounds. promoter ligands, carriers, and the concentrations of promoter ligands were varied as set forth in the examples and Table below.

After the addition of the above to the autoclave, the autoclave was sealed and mechanical stirring begun. The autoclave was flushed once with an 800 psi charge of carbon monoxide. The propylene was then added to the autoclave from a pre-weighed bomb and the amount of propylene added was measured by weight difference. Carbon monoxide was added to bring the pressure of the autoclave up to 450 psi. The temperature was then increased to the run temperature, and the time was recorded. Carbon monoxide was added to the reactor as needed after it reached run temperature and pressure by the use of a reservoir filled with carbon monoxide. A record of the rate of carbon monoxide addition was made using a pressure transducer attached to a recorder. After the reaction was completed, usually in about 40 minutes, the autoclave was cooled with cold running water. The entire volume of gas vented from the autoclave was collected in a multi-layered gas sampling bag, measured using a wet test meter, and a sample was injected into the Carle III gas analyzer. The liquid effluent was weighed and analyzed as set forth above.

The results of the reaction runs are reported in the Table below as follows.

$$\% \text{ Conversion} = \frac{\text{Moles of Product Observed} \times 100}{\text{Moles of Propylene Fed}}$$

$$\% \text{ Selectivity} = \frac{\text{Moles of Isobutyric Acid Produced} \times 100}{\text{Moles of All Products}}$$

The catalysts prepared in the below examples were run according to the procedure set forth above. The results of the reaction runs together with the amount of propylene fed and reaction time are reported in the Table. Unless noted differently in the Table, the reactions were run at a temperature of 110° C. and a carbon monoxide pressure of 800–1200 psi in about 100 ml acetic acid solvent. The molar ratio of water to propylene in the reaction mixture was maintained in a ratio of about 1.5:1 to about 2:1. The amount of palladium present on the carriers utilized in the reaction was about 5% by weight. The Table also notes the ligand and hydrogen halide used, as well as their molar ratios to the palladium in the catalyst system.

EXAMPLES 1–5

The palladium-carrier component of the catalyst utilized in Examples 1–5 was Palladium on Powdered Charcoal, commercially available from Matheson, Coleman and Bell of Norwood, Ohio, and consisted of 5% by weight palladium on carbon. Various stabilizing ligands were added to the reaction mix as reported in the Table. It can be noted from the results reported in the Table, the selectivity to isobutyric acid improved unexpectedly when the organo-arsine ligand was utilized. The palladium impregnated on the inert carbon carrier catalyst produced a good conversion to isobutyric acid, with excellent selectivity to the branched or "iso" isomer of butyric acid.

EXAMPLE 6

In Example 6, 0.51 grams of palladium acetate was dissolved in 10 ml $CHCl_3$. To this solution was added 10 grams Pittsburgh Activated Charcoal (available from Calgon Corp., Pittsburgh, Penna.) and dried at 125° C. for 25 minutes. The resulting solid was then cooled and 0.5 grams of 85% $H_3PO_4$ in 5 grams $H_2O$ was added. The total mass was heat treated at 125° C. for 18 hours, yielding the palladium impregnated carbon carrier catalyst, having 5% palladium by weight. As can be seen from the Table, this catalyst produced a good conversion with excellent selectivity to isobutyric acid.

EXAMPLE 7

The catalyst in Example 7 was prepared by dissolving 0.98 grams of palladium acetate in 20 ml of $CHCl_3$, and adding to this solution 20 grams of Pittsburgh Activated Charcoal. The solid was dried in a stream of air at ambient temperature for one hour and was then heat treated at 125° C. for 12 hours. The heat treated solid was then reduced for one hour at 175° C. by contacting the same with $H_2$ gas. As can be seen in the Table, the catalyst prepared in Example 7 exhibited a good conversion and excellent selectivity to isobutyric acid.

EXAMPLE 8

The palladium component of the catalyst utilized in Example 8 consisted of 5% Palladium on Alumina Powder, available from Oxy-Catalyst Inc., West Chester, Penna. This catalyst exhibited very good conversion and excellent selectivity to isobutyric acid as noted in the Table.

EXAMPLES 9-16

The supported palladium component of the catalyst in Examples 9-16 was prepared in the following manner. 1.37 grams palladium nitrate was dissolved in 30 ml distilled water. This solution was then used for a multiple impregnation of 10 grams of 13X Molecular Sieve zeolites (available from Supelco Company). The 10 gram sample of molecular sieve carriers was mixed with 10 ml of solution and dried one-half hour at 125° C. This impregnation step was repeated twice. Following the third impregnation and drying, the sample was calcined at 300° C. for one hour. The resulting solid was about 5% by weight palladium on molecular sieves. As can be seen from the results in the Table, the palladium impregnated molecular sieve zeolite catalysts exhibit an excellent conversion and selectivity to isobutyric acid.

EXAMPLES 17-20

For Examples 17-19, the palladium on carbon catalyst component was prepared as set forth in Example 7 above. In Example 17, 2.5 grams of the palladium-carbon carrier component was mixed with 5 ml of an aqueous solution containing 0.49 grams silver nitrate and was dried in a vacuum at 260° C. This solid was then mixed with a solution of 1 gram concentrated HCl in 5 grams of water, again with drying in a vacuum. The Ag/Pd impregnated carrier was then washed with 100 ml $H_2O$ and dried at 125° C. for four hours. The molar ratio of silver to palladium in this catalyst was about 2:1.

In Example 18, 2.5 grams of palladium on carbon was mixed with 5 ml of an aqueous solution containing 3 grams $HAuCl_4.3H_2O$. This solution was evaporated to dryness and thereafter heat treated at 125° C. for twelve hours. The dried Au/Pd impregnated carrier component was then reduced by heating for one hour at 175° C. in the presence of $H_2$ gas. The molar ratio of gold to palladium was about 2:1.

In Example 19, 2.5 grams of palladium impregnated carbon was saturated with 5 ml of an aqueous solution containing 0.89 grams thallium nitrate and was dried under vacuum. The solid was then mixed with a solution containing 2 grams concentrated HCl in 9 grams of water with stirring. The solid was then washed with 175 ml $H_2O$ and dried in a stream of air. The molar ratio of thallium to palladium in the impregnated carrier component was about 2.5:1.

The catalyst/carrier component in Example 20 was prepared by dissolving 0.263 grams palladium acetate and 0.31 grams $NH_4ReO_4$ in 1 ml $H_2O$ and 4 ml concentrated HCl with heating to about 80° C. To this solution was added 2.5 grams Pittsburgh Activated Charcoal with heating to about 80° C. The sample was then heat treated for about 12 hours at 125° C. Molar ratio of rhenium to palladium was about 1:1. The catalysts in Examples 17-20 exhibited a very good selectivity to isobutyric acid, as can be seen from the results in the Table.

As can be seen from the above Examples and Table, the hydrocarboxylation of propylene with carbon monoxide and water in the presence of a catalyst comprising palladium or a palladium compound supported on an inert carrier, an organo-arsine ligand compound and a hydrogen halide produces a high conversion to butyric acid, particularly with an unexpectedly high selectivity to isobutyric acid, generally of about 80% or greater.

Thus it should be apparent to those skilled in the art that the subject invention accomplishes the objects set forth above. It is to be understood that the subject invention is not to be limited by the examples set forth herein. These have been provided merely to demonstrate operability, and the selection of specific palladium salts, type of organo-arsine stabilizer/ promoter ligand, hydrogen halide, support materials, solvents and reaction conditions can be determined from the total specification disclosure provided without departing from the spirit of the invention herein disclosed and described, the scope of the invention including modifications and variations that fall within the scope of the attached claims.

TABLE

| Example No. | Catalyst & Mole Ratio | Time Run (Minutes) | Grams Fed (Propylene) | Isobutyric Acid % Conv. | % Selectivity |
|---|---|---|---|---|---|
| 1. | Pd on C/Sb$\phi_3$/HCl<br>1    2    90 | 90 | 14.43 | Trace | 72 |
| 2. | Pd on C/P$\phi_3$/HCl<br>1    2    90 | 90 | 14.65 | 22.1 | 73.8 |
| 3. | Pd on C/As$\phi_3$/HCl<br>1    2    90 | 90 | 14.75 | 15.4 | 82.8 |
| 4. | Pd on C/As$\phi_3$/HCl<br>1    4    90 | 60 | 14.36 | 40.5 | 80.5 |
| 5. | Pd on C/As$\phi_3$/HCl<br>1    4    90 | 60 | 14.63 | 58.7 | 81.0 |
| 6. | PdPO$_4$ on C/As$\phi_3$/HCl<br>1    4    90 | 90 | 14.27 | 40.7 | 79.6 |
| 7. | Pd(OAc)$_2$ on C/As$\phi_3$/HCl<br>1    4    90 | 90 | 14.44 | 34.4 | 78.6 |
| 8. | Pd on Al$_2$O$_3$/As$\phi_3$/HCl | 90 | 14.79 | 67.5 | 80.5 |

TABLE-continued

| Example No. | Catalyst & Mole Ratio | | | Time Run (Minutes) | Grams Fed (Propylene) | Isobutyric Acid % Conv. | % Selectivity |
|---|---|---|---|---|---|---|---|
| | 1 | 4 | 90 | | | | |
| 9. | Pd on Z/Asφ3/HCl | | | 60 | 14.98 | 85.3 | 80.8 |
| | 1 | 4 | 90 | | | | |
| 10. | Pd on Z/Asφ3/HCl | | | 60 | 14.88 | 82.2 | 80.4 |
| | 1 | 4 | 90 | | | | |
| 11. | Pd on Z/Asφ3/HCl | | | 60 | 15.14 | 79.2 | 81.0 |
| | 1 | 4 | 90 | | | | |
| 12.* | Pd on Z/Asφ3/HCl | | | 120 | 27.31 | 54.8 | 85.5 |
| | 1 | 4 | 90 | | | | |
| 13. | Pd on Z/Asφ3/HCl | | | 90 | 26.9 | 52.2 | 86.6 |
| | 1 | 4 | 90 | | | | |
| 14. | Pd on Z/Asφ3/HCl | | | 90 | 28.06 | 55.9 | 83.4 |
| | 1 | 4 | 90 | | | | |
| 15.** | Pd on Z/Asφ3/HCl | | | 100 | 27.83 | 47.5 | 80.1 |
| | 1 | 4 | 90 | | | | |
| 16. | Pd on Z/Asφ3/H2S/HCl | | | 90 | 14.67 | 79.5 | 80.2 |
| | 1 | 4 | 1 | 90 | | | |
| 17. | Ag/Pd on C/Asφ3/HCl | | | 85 | 14.15 | 33.4 | 75.1 |
| | 2 1 | 4 | 90 | | | | |
| 18. | Tl/Pd on C/Asφ3HCl | | | 60 | 14.18 | 11.1 | 79.7 |
| | 2.5 1 | 4 | 90 | | | | |
| 19. | Au/Pd on C/Asφ3/HCl | | | 90 | 14.70 | 42.5 | 79.8 |
| | 2 1 | 4 | 90 | | | | |
| 20. | Re/Pd on C/Asφ3/HCl | | | 60 | 14.5 | 14.6 | 79.2 |
| | 1 1 | 4 | 90 | | | | |

*Reaction temperature 50°-100° C.
**Calcined at 900° C.

We claim:

1. A process for the selective hydrocarboxylation of propylene to produce butyric acid in the liquid phase at a temperature of about 75° C. to 150° C. and a pressure of about 250 psi to about 5000 psi, wherein the isobutyric acid isomer product predominates, comprising forming a reaction mixture or propylene, carbon monoxide and water in the presence of a catalyst comprising palladium in a valance state of zero supported on an at least partially porous inert carrier, a hydrogen halide and an organo-arsine ligand.

2. A process as recited in claim 1, wherein the reaction is carried out at a temperature of about 90° C. to about 125° C.

3. A process as recited in claim 1, wherein the pressure is maintained at about 400 psi to 1200 psi.

4. A process as recited in claims 1 or 3 wherein said pressure is exerted substantially by carbon monoxide.

5. A process as recited in claim 1 wherein said inert carrier is selected from the group consisting of silica, alumina, alumina-silica, silicon carbide, titania, zirconia, carbon, and zeolites.

6. A process as recited in claim 1 wherein said inert carrier is alumina.

7. A process as recited in claim 1 wherein said inert carrier is alumina-silica.

8. A process as recited in claim 1 wherein said inert carrier is carbon.

9. A process as recited in claim 1 wherein said inert carrier is activated charcoal.

10. A process as recited in claim 1 wherein said inert carrier is a zeolite.

11. A process as recited in claim 1 wherein said inert carrier is a molecular sieve zeolite.

12. A process as recited in claim 1 wherein said inert carrier is a type X molecular sieve zeolite.

13. A process as recited in claim 1 wherein said organoarsine is represented by the formula

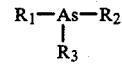

wherein $R_1$, $R_2$ and $R_3$ are independently a substituted or nonsubstituted alkyl, aryl, alkoxy or aryloxy and at least one R is an aryl or substituted aryl group stable at reaction temperatures and pressures, wherein substituents are selected from the group consisting of lower alkyl, alkoxy carbonyl, halide and cyanide, and wherein said substituent is in at least one of the meta and para positions.

14. A process as recited in claim 13 wherein said organoarsine is a triarylarsine.

15. A process as recited in claim 14 wherein said triarylarsine is triphenylarsine.

16. A process as recited in claim 1 wherein said hydrogen halide is selected from the group HCl, HBr and HI.

17. A process as recited in claim 1 wherein said hydrogen halide is HCl.

18. A process as recited in claim 17 wherein a strong acid in addition to HCl is included in the reaction mixture.

19. A process as recited in claim 18 wherein said strong acid is selected from the group consisting of HBr, HI, $H_2S$, $H_2SO_4$, HCN, $H_3PO_4$ and $HBF_4$.

20. A process as recited in claim 1 wherein said reaction mixture includes an inert organic solvent.

21. A process as recited in claim 20 wherein said inert organic solvent is selected from the group consisting of benzene, carboxylic acids, esters, ethers, aldehydes, ketones and mixtures thereof.

22. A process as recited in claim 20 wherein said solvent comprises a carboxylic acid.

23. A process as selected in claim 22 wherein said solvent is acetic acid.

24. A process as recited in claim 22 wherein said solvent is butyric acid.

25. A process as recited in claim 1 wherein the molar ratio of propylene to palladium is about 10:1 to about 2000:1.

26. A process as recited in claim 1 wherein the molar ratio of propylene to palladium is about 100:1.

27. A process as recited in claim 1 wherein the molar ratio of organoarsine to palladium is about 1:1 to about 100:1.

28. A process as recited in claim 1 wherein the molar ratio of organoarsine to palladium is about 2:1 to about 20:1.

29. A process as recited in claim 1 wherein the molar ratio of hydrogen halide to palladium is about 5:1 to about 500:1.

30. A process as recited in claim 1 wherein the molar ratio of hydrogen halide to palladium is about 45:1 to about 90:1.

31. A process as recited in claim 17 or 18 wherein the molar ratio of HCl to palladium is about 5:1 to about 500:1.

32. A process as recited in claim 17 or 18 wherein the molar ratio of HCl to palladium is about 45:1 to about 90.1.

33. A process as recited in claim 1 wherein said water to propylene ratio is about 0.01:1 to about 2:1.

34. A process as recited in claim 1 wherein said water to propylene ratio is about 1:1 to about 2:1.

35. A process as recited in claim 1 wherein said water to propylene ratio is about 1.5:1.

36. A process as recited in claim 1 wherein said catalyst further comprises a metal or metal-containing compound in addition to said palladium, said additional metal being selected from the group consisting of metals from Periodic table groups VIIA, VIII, IB and IIIB.

37. A process as recited in claim 36 wherein said metal or metal component of said metal-containing compound is selected from the group consisting of rhenium. silver, gold and thallium.

38. A process as recited in claim 36 or 37 wherein the molar ratio of said metal or metal-containing compound to palladium is about 0.5:1 to about 5.0:1.

39. A process as recited in claims 36 or 37 wherein the molar ratio of said metal or metal-containing compound is about 1:1 to about 2.5:1.

* * * * *